(12) United States Patent  
Rao et al.

(10) Patent No.: US 8,804,909 B2
(45) Date of Patent: Aug. 12, 2014

(54) SYSTEM AND METHOD FOR REGULATING DATA ACQUISTION

(75) Inventors: Naresh Kesavan Rao, Clifton Park, NY (US); Richard Gordon Cronce, New Berlin, WI (US); German Guillermo Vera, Menomonee Falls, WI (US); Jianjun Guo, Ballston Spa, NY (US)

(73) Assignee: General Electric Company, Niskayuna, NY (US)

( * ) Notice: Subject to any disclaimer, the term of this patent is extended or adjusted under 35 U.S.C. 154(b) by 399 days.

(21) Appl. No.: 13/340,175

(22) Filed: Dec. 29, 2011

(65) Prior Publication Data

US 2013/0170622 A1  Jul. 4, 2013

(51) Int. Cl.  
*H05G 1/56* (2006.01)  
*H01J 31/50* (2006.01)

(52) U.S. Cl.  
USPC .......... 378/98.8; 378/189; 378/204; 378/901; 250/370.09

(58) Field of Classification Search  
USPC .................. 378/91–98.8, 189, 204, 210, 901; 250/370.01, 370.09  
See application file for complete search history.

(56) References Cited

U.S. PATENT DOCUMENTS

| 7,053,806 B1 | 5/2006 | Rao et al. |
| 7,211,803 B1 | 5/2007 | Dhurjaty et al. |
| 7,254,261 B2 | 8/2007 | Avinash et al. |
| 7,570,185 B2 | 8/2009 | Rao et al. |
| 2010/0013560 A1 | 1/2010 | Rao et al. |
| 2010/0215146 A1 | 8/2010 | Rao et al. |

*Primary Examiner* — Anastasia Midkiff  
(74) *Attorney, Agent, or Firm* — Jeinfer E. Haeckl (57) ABSTRACT

A method for regulating the acquisition of an analog input signal from a digital X-ray panel is provided. The method includes opening a switch disposed between an integrator and the digital X-ray panel prior to an integrator event or upon detection of a fault in the digital X-ray panel to decouple the integrator from the digital X-ray panel, wherein the integrator is configured to integrate the analog input signal from the digital X-ray panel. Also, a system for data acquisition is provided. Further, a method for fault protection of the digital X-ray panel is provided.

25 Claims, 5 Drawing Sheets

SYSTEM AND METHOD FOR REGULATING DATA ACQUISTION

BACKGROUND

A number of radiological imaging systems of various designs are known and are presently in use. Certain of these systems are based upon generation of X-rays that are directed toward a subject of interest. The X-rays traverse the subject and, in digital imaging systems, impact a digital detector. Such X-ray systems use digital circuitry for detecting the X-rays, which are attenuated, scattered or absorbed by the intervening structures of the subject. In medical diagnostic contexts, for example, such systems may be used to visualize internal tissues and diagnose patient ailments. In other contexts, parts, baggage, parcels, and other subjects may be imaged to non-invasively assess their contents and for other purposes.

Individual pixels of an X-ray panel of the digital detector store a charge representative of an amount of incident X-ray radiation received by each pixel. Circuitry (e.g., front-end circuitry) coupled to the X-ray panel regulates signal acquisition by individually accessing and integrating the charge from each pixel. However, certain events during signal acquisition may hinder this regulation by the circuitry resulting in image artifacts within a generated X-ray image. For example, charge dumping from the front-end circuitry to the panel or a fault within the panel may induce crosstalk between components of the panel resulting in the image artifacts.

BRIEF DESCRIPTION

In a first embodiment, a method for regulating the acquisition of an analog input signal from a digital X-ray panel is provided. The method includes opening a switch disposed between an integrator and the digital X-ray panel prior to an integrator event or upon detection of a fault in the digital X-ray panel to decouple the integrator from the digital X-ray panel, wherein the integrator is configured to integrate the analog input signal from the digital X-ray panel.

In a second embodiment, a digital acquisition system is provided. The system includes a digital X-ray panel configured to acquire X-ray image data, wherein the digital X-ray panel comprises multiple pixels configured to store a charge. The system also includes, for each pixel, an integrator configured to integrate an analog input signal representative of the charge stored on the respective individual pixel. The system further includes, for each integrator, a switch disposed between the respective integrator and the digital X-ray panel, wherein the switch is configured to open to decouple the respective integrator from the digital X-ray panel prior to reset of the respective integrator or upon detection of a fault in the digital X-ray panel.

In a third embodiment, a method for fault protection of a digital X-ray panel is provided. The method includes detecting a fault in a data line of the digital X-ray panel. The method also includes opening a switch disposed between an integrator and the digital X-ray panel to decouple the integrator from the digital X-ray panel, wherein the integrator is configured to integrate the analog input signal from the digital X-ray panel.

BRIEF DESCRIPTION OF THE DRAWINGS

These and other features and aspects of the present embodiments will become better understood when the following detailed description is read with reference to the accompanying drawings in which like characters represent like parts throughout the drawings, wherein.

DETAILED DESCRIPTION

In the subsequent paragraphs, various aspects of regulating data or signal acquisition will be explained in detail. The various aspects of the present techniques will be explained, by way of example only, with the aid of figures hereinafter. The present techniques for regulating signal acquisition will generally be described by reference to an exemplary digital X-ray system designated by numeral 10. However, the technique may find application in a range of settings and systems, and its use in the X-ray system shown is but one such application.

Figure 1:
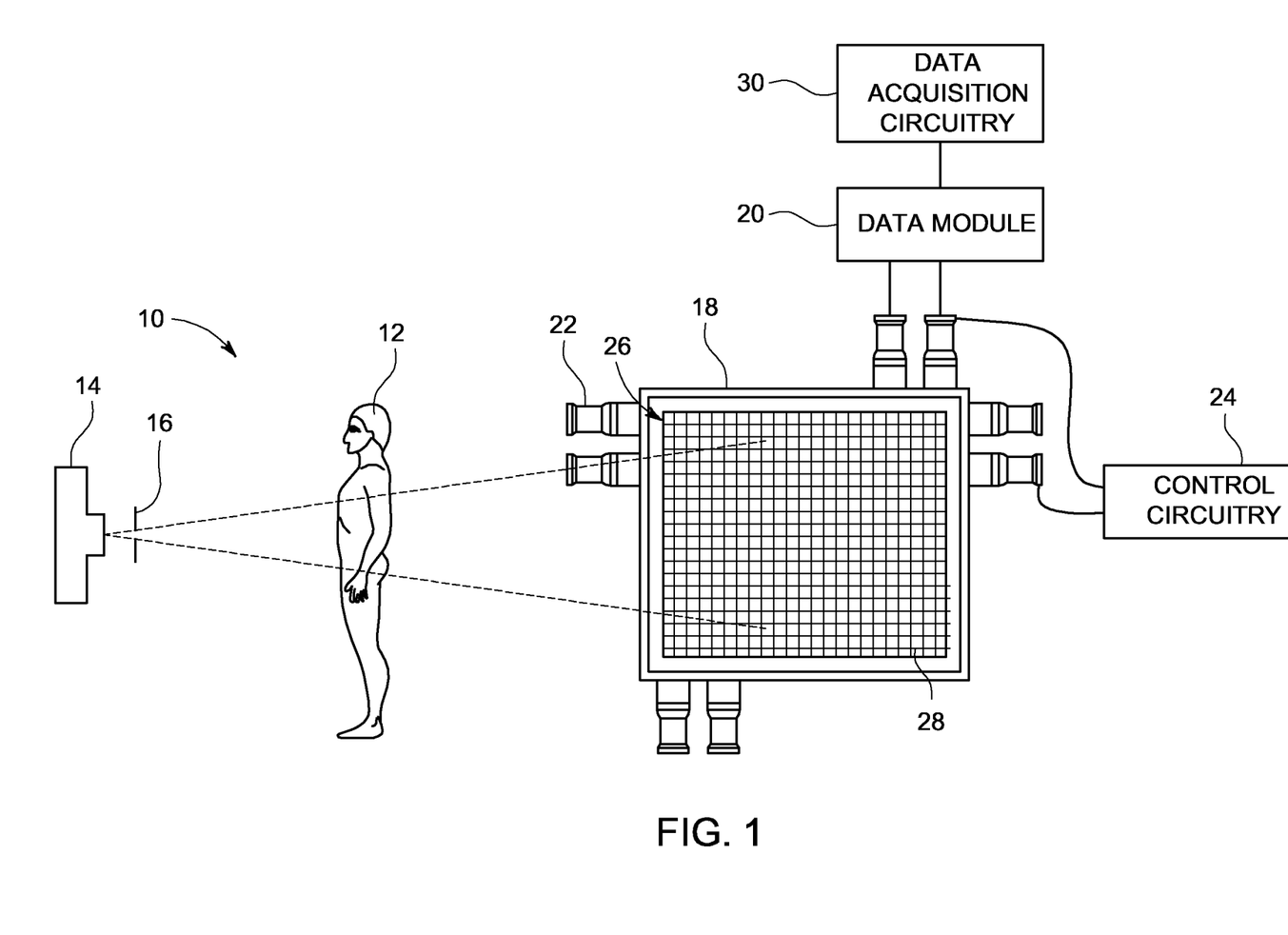
FIG. 1 is a diagrammatic view of an exemplary digital X-ray system, in which regulation of signal acquisition from a digital X-ray panel is implemented in accordance with certain embodiments of the present disclosure.

The digital X-ray system 10 of FIG. 1 is operable to capture an X-ray projection of a portion of a body of a subject 12 under medical examination. However, as will be appreciated by those skilled in the art, the digital X-ray system 10 may also be utilized for non-destructive evaluation (NDE) of materials, such as castings, forgings, or pipelines, inspection of parts, parcels and baggage, and other such applications. The digital X-ray system 10 comprises an X-ray source 14 that is used to scan the subject 12. The X-ray source 14 generates X-ray beams that pass through a collimator 16 and then penetrate through the subject 12. In a typical medical application, the X-ray beams may be attenuated based on the density of the organs, skin, lesions, muscle, bones and the like, in the various portions of the body of the subject 12. The attenuated X-rays strike a digital X-ray panel 18, as illustrated in FIG. 1, which comprises a plurality of photodiodes that form a pixel array. The panel 18 is read row-by-row or column-by-column by one or more data modules 20, where each line of pixels may be enabled for scanning, by one or more scan modules 22. Control circuitry 24 is used to control the operation of the data modules 20 and the scan modules 22.

The digital X-ray panel 18 comprises a plurality of rows 26, each of which contains a plurality of pixels 28 arranged contiguously to form a pixel matrix or a pixel array. In embodiments, each pixel includes a radiation detection element such as a photodiode. During operation of the X-ray panel 18, received X-ray radiation is converted to a lower energy form such as optical photons detectable by the photodiodes, and each of the pixel photodiodes has an initial charge that is depleted by an amount representative of the amount of X-ray radiation incident on the respective location of each pixel 28. The data modules 20 read the amount of charge from each of the pixels 28. Each row 26 is scanned by the data modules 20 in conjunction with the scan modules 22 to read the amount of charge from all the pixels 28 in that row 26 (or column). The scan module 22 corresponding to a row 26 enables reading the pixels 28 in that row 26. When the pixel 28 is enabled for reading, the data module 20 corresponding to that pixel 28 reads the charge stored on the photodiode or pixel 28 by recharging the photodiode. Having read the charge value from the plurality of pixels 28, the data module 20 converts the charge value into a digital equivalent that is sent to data acquisition circuitry 30 for further processing, such as generating a radiological image or projection, for example.

The digital x-ray system 10 may be a radiography system, mammography system, fluoroscopy system, or may be a system that combines the functionality of several X-ray applications. As discussed above, the energy intensity of the X-ray source 14 may vary according to which application is being employed in the digital x-ray system 10. The data modules 20 described herein may be used with a variety of X-ray applications regardless of the X-ray energy intensity employed. This allows one data module to be used in a variety of imaging systems, resulting in higher economies of scale and reduced production costs.

Figure 2:
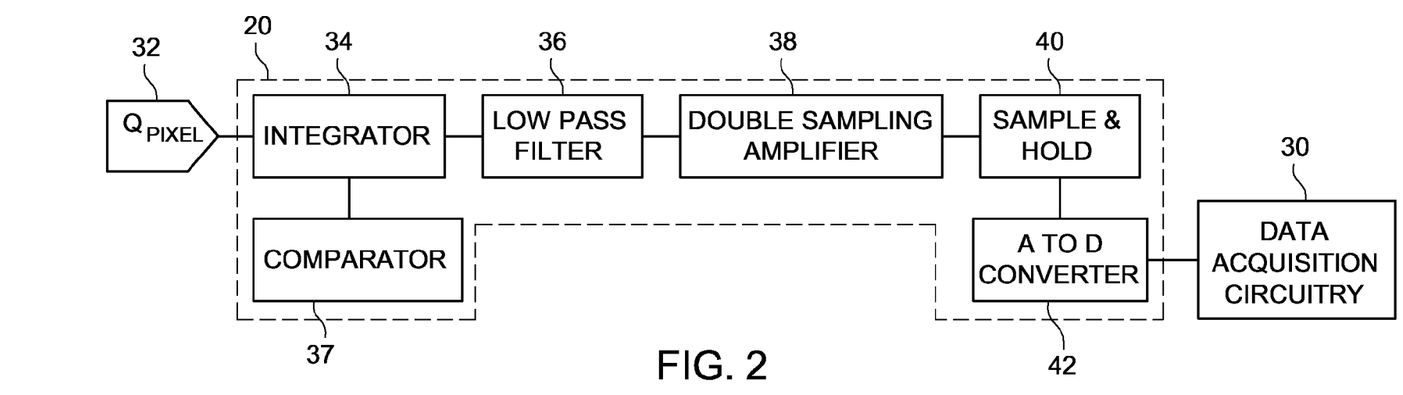
FIG. 2 is a diagrammatic view of an exemplary digital conversion system for the digital X-ray system shown in FIG. 1 with improved regulation of signal acquisition in accordance with certain embodiments of the present disclosure.

FIG. 2 is a diagrammatic view of the exemplary digital conversion system (e.g., data module 20 or analog readout chip (ARC)) in accordance with certain embodiments. Each data module 20 is configured to read an input pixel charge 32 (e.g., analog input signal) from a photodiode coupled to the pixel 28 and provide the digital equivalent to the data acquisition circuitry 30. In some embodiments, the data module 20 may include several processing channels or data lines, each coupled to an individual pixel 28 and configured to process the pixel charge 32 from the respective pixel 28. The data acquisition circuitry 30 receives the digital data from the data modules 20 and processes the data to form an image. In the depicted embodiment, each data module 20 comprises an integrator 34, which integrates the pixel charge 32 for conversion into an equivalent voltage value which is fed into a low-pass-filter 36 (LPF) for reducing noise. In certain embodiments, a comparator 37 may be coupled to the integrator 34. The comparator 37 may monitor the data line or channel being integrated for a fault (e.g., fault current) between a bias voltage and the data line or one of the scan voltages and the data line. For example, the comparator 37 may detect whether the voltage output of the data line moves closer to the voltage rails due to a fault. If the voltage output of the data approaches the voltage rails, the comparator 37 fires to generate a signal indicative of a fault to begin fault protection measures described in greater detail below.

The voltage signal output from the low-pass filter 36 is fed into a double sampling amplifier (DSA) 38. The output of the DSA 38 is sampled and held in a sample-and-hold (S/H) circuit 40. The output of the S/H circuit 40 may be fed into an analog to digital converter (ADC) 42 that converts the measured analog signal(s) to a digital format and sends the data to the data acquisition circuitry 30 for further processing. The ADC 42 may be any suitable analog to digital converter. In some embodiments, the ADC 42 may include a comparator, a digital to analog converter (DAC), a counter, and a register. In certain embodiments, the comparator provides either a high or a low output based on a comparison of the voltage output of the S/H circuitry 40 and a comparison signal provided by the DAC. The register is provided with a counter value from the counter that is proportional to the digital code provided to the DAC for generating the comparison signal. The counter value and the digital code provided to the DAC are both incremented over time so that the comparison signal gradually increases. The output of the comparator may be configured to freeze the counter value in the register when the output of the S/H circuit 40 and the comparison signal are equal. Because the counter value provided to the DAC and the register is proportional, the frozen counter value in the register is representative of the digitized output of the input pixel charge 32 of the corresponding pixel 28. The starting point of the comparison signal will therefore determine, in part, how quickly the output of the S/H circuit 40 may be digitized.

It may be noted that the integrator 34, the low-pass filter 36, the comparator 37, the DSA 38, the S/H circuit 40 and the ADC 42 may comprise a single channel or data line that reads a single photodiode or pixel 28. Each data module 20 may include several such channels or data lines. In some embodiments, the data module may include enough channels to enable the reading and digitizing of P pixels simultaneously. Thus, if a row of M pixels has to be read simultaneously, M/P data modules 20 may be employed.

The integrator 34 regulates accessing and integrating the charge from an individual pixel 28 via an associated data line. The circuit described above may be subject to certain events that interfere with the integrator's regulation of the data line and that may result in crosstalk between components (e.g., between data lines via a common electrode) of the digital X-ray panel 18 and image artifacts in images generated from the acquired X-ray image data. For example, switching between pixels of a data line, saturation of the integrator 34, or a fault in the digital X-ray panel 18 may hinder the regulation of acquiring the charge (e.g., analog input signal) from the pixel 28. As will be described below, embodiments of the present techniques successfully reduce image artifacts by regulating the interface between the front-end circuitry (e.g., data modules 20 or ARC) and the X-ray panel 18 in response to these events. In addition, the present techniques enable additional signal processing to reduce noise (e.g., due to digitization).

Figure 3:
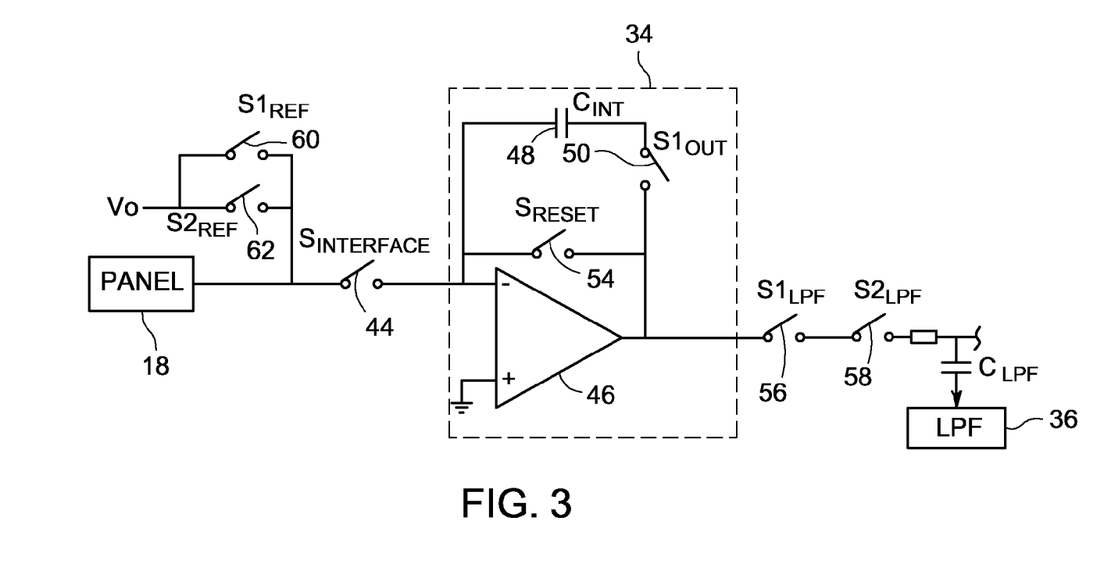
FIG. 3 is a detailed diagrammatic view of an integrator and an interface between the integrator and the digital X-ray panel of FIG. 1 (e.g., to prevent charge dumping into the digital X-ray panel) in accordance with certain embodiments of the present disclosure.

FIG. 3 is a detailed diagrammatic view of the integrator 34 and an interface between the integrator 34 and the digital X-ray panel 18 (e.g., to prevent charge dumping into the digital X-ray panel) illustrating one technique for regulating data or signal acquisition in response to an integrator event (e.g., integrator reset due to switching between pixels of a data line or integrator saturation) to reduce image artifacts. In this embodiment, the digital X-ray panel 18 (e.g., via a data line associated with an individual pixel 28) is coupled to the input of integrator 34 by an interface switch 44, $S_{interface}$, disposed between the panel 18 and the integrator 34. As mentioned above, a pixel charge may be held in each photodiode or pixel 28. During integration of the charge (e.g., analog input signal) from the pixel 28 to the integrator 34, the interface switch 44 is on (i.e., closed) coupling the detector panel 18 and integrator 34. However, prior to an integrator event (i.e., integrator reset) caused by switching between pixels of a data line or saturation of the integrator 34, the interface switch 44 is off (i.e., open). In certain embodiments, the interface switch 44 may turned off (i.e., opened) in response to the detection of a fault in the X-ray panel 18.

Thus, the integrator 34 integrates the analog input signal prior to opening of the interface switch 44. In addition, as described in detailed below, the integrator 34 may provide an output based on the analog input signal for digitization after opening of the interface switch 44 to reduce digitization noise.

Opening of the interface switch 44 blocks crosstalk across the digital X-ray panel 18 (e.g., between data lines coupled via a common electrode). Blocking crosstalk between components of the digital X-ray panel 18 reduce images artifacts in images generated from X-ray image data (e.g., analog input signal). In addition, opening of the interface switch 44 blocks charge dumping from the integrator to the digital X-ray panel 18. Further, as described in detail below, the interface switch 44 enables additional signal processing of the output of the integrator 34. The interface switch 44 is designed to provide an ON resistance of approximately 100 Ohm or less. In addition, the interface switch 44 provides additional electrostatic discharge protection between the panel 18 and the front-end circuitry due to junctions formed between the panel 18 and the integrator 34 via the switch 44. The data line from the panel 18 may be coupled to a reference voltage (VO) (e.g., known reference voltage), via switches 60 ($S1_{ref}$) and 62 ($S2_{ref}$), after opening of the interface switch 44 and prior to reset of the integrator 34.

In the embodiment depicted, the integrator 34 comprises an operational amplifier (op-amp) 46 with an integration capacitor 48 ($C_{int}$) in a feedback loop. The capacitor 48 is coupled to the negative input terminal of the op-amp 46. Additionally, the capacitor 48 may be coupled to the output of the op-amp 44 (i.e., in feedback mode), via the switches 50 ($S1_{out}$). When the capacitor 48 is coupled to the output of the op-amp 46, the capacitor 48 amplifies the voltage output of the op-amp 46 and stores a charge that is proportional to the pixel charge. The integrator 34 also includes a reset switch 54 ($S_{reset}$) that is used to reset the integrator 34 to an initial condition wherein the output of the integrator is set to the ground voltage. Reset of the integration 34 occurs upon switching prior to charge acquisition from the next pixel on the data line of the digital X-ray panel 18 or saturation of the integrator 34. Reset of the integrator 34 occurs upon switching between pixels of the data line of the digital X-ray panel 18 or saturation of the integrator 34. Further, the output of the integrator 34 may be coupled to the LPF 36 via the switches 56 ($S1_{lpf}$) and 58 ($S2_{lpf}$). The switches 44, 50, 54, 56, 58, 60, and 62 may be controlled by the control circuitry 24 shown in FIG. 1.

Figure 4:
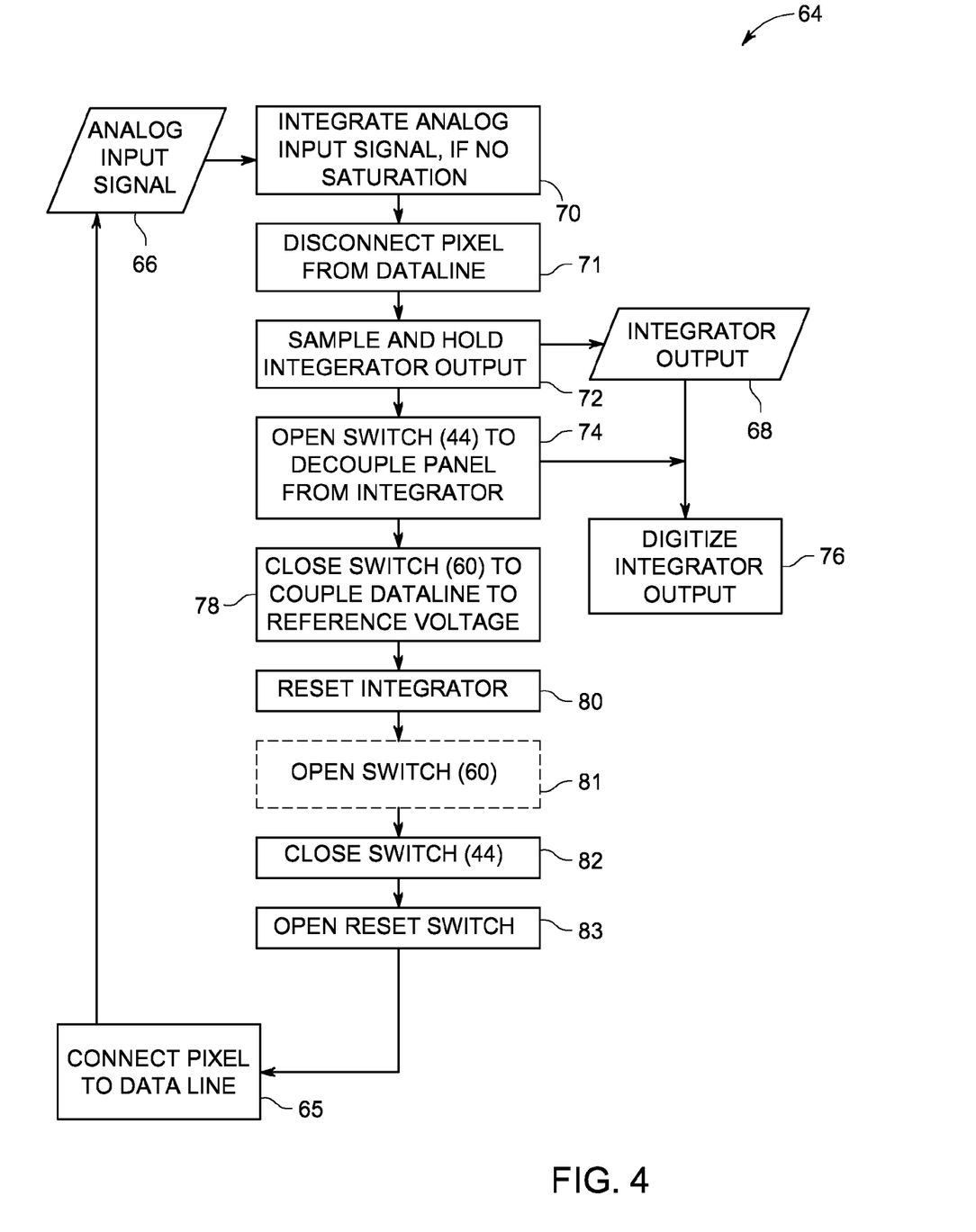
FIG. 4 is a flow chart illustrating a method for regulating an acquisition of an analog input signal from the digital X-ray panel of FIG. 1 (e.g., prior to switching between data lines) in accordance with certain embodiments of the present disclosure.

Regulation of the acquisition of an analog input signal from the digital X-ray panel 18, via the interface switch 44 and the integrator 34 described above, may occur in response to switching between pixels within a data line or integrator saturation due to a large signal from the pixel. FIG. 4 is a flow chart illustrating a method 64 for regulating the acquisition of an analog input signal from the digital X-ray panel 18 in response to switching between pixels of a data line. The method 64 includes connecting the pixel 28 to a data line (block 65). The method 64 also includes the integrator 34 integrating an analog input signal 66 from the digital X-ray panel 18 (e.g., via the data line coupled to the individual pixel 28) prior to opening of the interface switch 44 to generate an integrator output 68, if no saturation of the integrator 34 occurs (block 70). After integrating the signal 66, the method 64 includes disconnecting the pixel 28 from the data line (block 71) and sampling and holding the integrator output from 68 acquired from the pixel 28 (block 72). Switching between pixels 28 of the data line triggers an integrator event (i.e., integrator reset). Prior to the integrator event, control circuitry 24 opens the interface switch 44 to decouple the panel 18 (e.g., data line) from the integrator 34 (block 74).

Opening of the interface switch 44 blocks charge dumping from the integrator 34 to the panel 18 due to the reset of the integrator 34. Opening of the interface switch 44 also blocks crosstalk across the digital X-ray panel 18 (e.g., between data lines coupled via a common electrode) due to charge dumping and, thus, reduces image artifacts in generated images.

In addition, opening of the interface switch 44 enables additional signal processing of the analog input signal 66 acquired by the integrator 34. The integrator 34 acts as a memory device by storing the charge from the pixel 28 in the panel 18. After opening of the interface switch 44, the integrator output 68 may be digitized and N times (block 76) and averaged. Digitizing the integrator output 68 by N times reduces digitization noise by $\sqrt{N}$. Opening of the interface switch 44 reduces contamination (e.g., panel charge retention currents) from the panel 18. In addition, if the charge (i.e., analog input signal 66) acquired by the integrator 34 is small enough, the signal 66 may be amplified via voltage amplification by redistributing the charge from a larger capacitor (e.g., op-amp 46) to a smaller capacitor (e.g., capacitor 48) to further reduce digitization noise. Integrating the analog input signal from the digital X-ray panel prior to opening of the switch and averaging multiple readings of an output of the integrator based on the analog output signal after opening of the switch reduces digitization noise.

After opening of the switch interface 44, the data line is coupled to the reference voltage (VO) (block 78), prior to reset of the integrator 34, by closing switches 60. After coupling of the data line to the reference voltage (block 78), the method 64 includes resetting the integrator 34 (block 80) by closing switch 54. In certain embodiments, the method 64 includes opening switches 60 (block 81). A transient period after the integrator reset, the switch 44 may be closed (block 82) prior to the next integration by the integrator 34. The method 64 further includes opening the reset switch 54 prior to the next integration (block 83).

Figure 5:
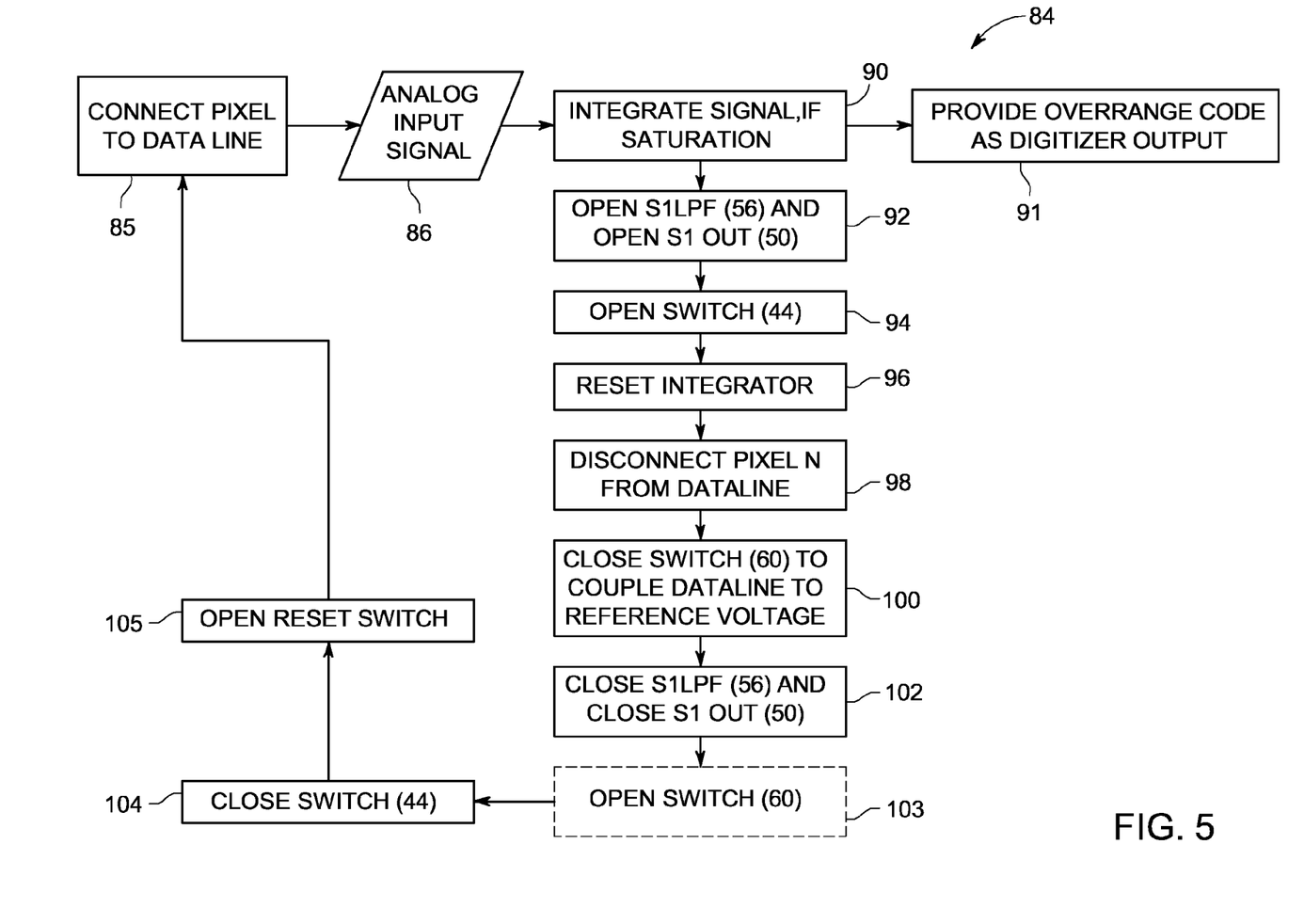
FIG. 5 is a flow chart illustrating a method for regulating an acquisition of an analog input signal from the digital X-ray panel of FIG. 1 (e.g., in response to a saturation event) in accordance with certain embodiments of the present disclosure.

FIG. 5 is a flow chart illustrating a method 84 for regulating the acquisition of an analog input signal from the digital X-ray panel 18 in response to integrator saturation. The method 84 includes connecting the pixel 28 to the data line (block 85). The method 84 also includes the integrator 34 integrating an analog input signal 86 from the digital X-ray panel 18 (e.g., via the data line coupled to the individual pixel 28) prior to opening of the interface switch 44, if saturation of the integrator 34 occurs (block 90). If the integrator 34 is saturated, the method 84 includes providing an overrange code as the digitizer output (block 91). In addition, saturation of the integrator due to the acquired signal 86 triggers an integrator event (i.e., integrator reset). Prior to the integrator event, control circuitry 24 decouples the integrator 34 from the LPF 36 by opening switches 56 and decouples the feedback capacitor 48 from the integrator 34 prior to the integrator event by opening switch 50 (block 92). In other words, the method 84 includes decoupling the integrator 34 from other circuits which store a signal proportional to the output of the integrator 34. After decoupling the integrator 34 from the other circuits, the method 84 includes opening the interface switch 44 to decouple the panel 18 (e.g., data line) from the integrator 34 (block 94). Opening of the interface switch 44 blocks dump charging from the integrator 34 to the panel 18 due to the reset of the integrator 34. Opening of the interface switch 44 also blocks crosstalk across the digital X-ray panel 18 (e.g., between data lines coupled via a common electrode) due to charge dumping and, thus, reduces image artifacts in generated images. The method 84 then includes resetting the integrator 34 (block 96) by closing switch 54. After reset of the integrator 34, the method 84 includes disconnecting the pixel 28 from the data line (block 98).

After disconnecting the pixel 28 from the data line, the data line is coupled to the reference voltage (VO) (block 100) by closing switch 60. After coupling of the data line to the reference voltage (block 100), the method 84 includes closing switches 50 and 56 (block 102). In certain embodiments, the method 84 includes opening switch 60 (block 103) after closing switches 50 and 56. A transient period after the integrator reset, the switch 44 may be closed (block 104) prior to the next integration by the integrator 34. The method 84 further includes opening the reset switch 54 prior to the next integration (block 105).

Figure 6:
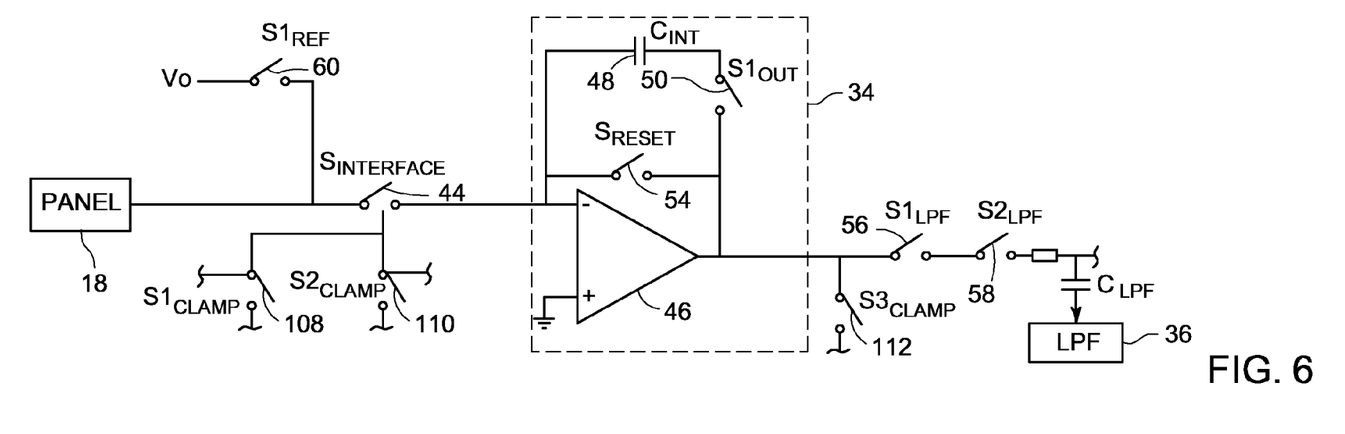
FIG. 6 is a detailed diagrammatic view of an integrator and an interface between the integrator and the digital X-ray panel of FIG. 1 (e.g., for fault protection) in accordance with certain embodiments of the present disclosure.

Besides an integrator event, the interface switch 44 may be used in fault protection of the digital X-ray panel 18. FIG. 6 is a detailed diagrammatic view of the integrator 34 and an interface between the integrator 34 and the digital X-ray panel 18 illustrating one technique for regulating data or signal acquisition in response to a detected fault in the panel 18. In this embodiment, the digital X-ray panel 18 (e.g., via a data line associated with an individual pixel 28) is coupled to the input of integrator 34 by the interface switch 44, $S_{interface}$, disposed between the panel 18 and the integrator 34. As mentioned above, a pixel charge may be held in each photodiode or pixel 28. During integration of the charge (e.g., analog input signal) from the pixel 28 to the integrator 34, the interface switch 44 is on (i.e., closed) coupling the detector panel 18 and integrator 34. However, in response to a detected fault via a signal, for example, from the comparator 37 shown in FIG. 2, the interface switch 44 is off (i.e., open).

Opening of the interface switch 44 blocks crosstalk across the digital X-ray panel 18 (e.g., between data lines coupled via a common electrode). Blocking crosstalk between components of the digital X-ray panel 18 reduces images artifacts in images generated from X-ray image data (e.g., analog input signal). The interface switch 44 is as described above in FIG. 3. The data line from the panel 18 may be coupled to the reference voltage (VO), via switches 60 ($S1_{ref}$), after opening of the interface switch 44 and prior to reset of the integrator 34.

The integrator 34 depicted in FIG. 6 is as described in FIG. 3. The interface switch 44 is coupled to the comparator 37 via switches 108 ($S1_{clamp}$) and 110 ($S2_{clamp}$). The output of the integrator 34 is coupled to the comparator 37 via a switch 112 ($S3_{clamp}$). In response to a signal from the comparator 37 of a detected fault in the detector panel 18 (e.g., fault in the data line), switches 108, 110, and 112 may be closed resulting in the opening of the interface switch 44, the clamping of the output of the integrator 34 (i.e., closing switches 56 and 58), and the resetting of the integrator 34. The switches 44, 50, 54, 56, 58, 60, 108, 110, and 112 may be controlled by the control circuitry 24 shown in FIG. 1.

Figure 7:
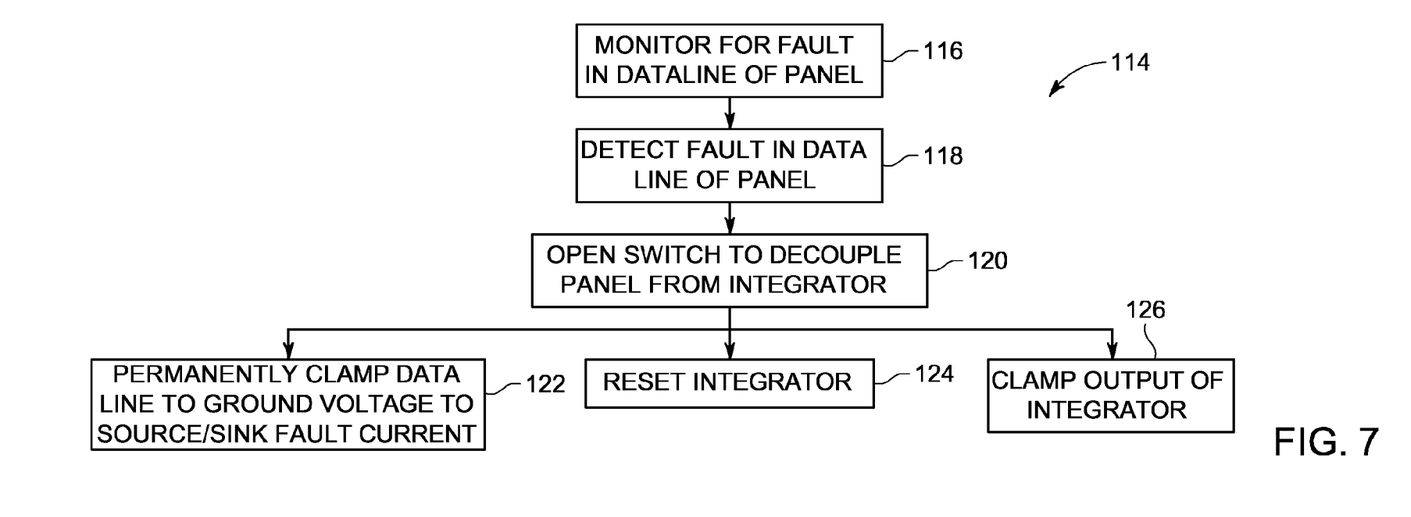
FIG. 7 is a flow chart illustrating a method for fault protection of a digital X-ray panel in accordance with certain embodiments of the present disclosure.

FIG. 7 is a flow chart illustrating a method 114 for fault protection of the digital X-ray panel 18. The method 114 includes monitoring the panel 18 (e.g., data line) for a fault (block 116). As mentioned above, the comparator 37 may monitor the data line or channel being integrated for a fault (e.g., fault current) between a bias voltage and the data line or one of the scan voltages and the data line. For example, the comparator 37 may detect whether the voltage output of the data line moves closer to the voltage rails due to a fault. The method 114 also includes detecting a fault in the data line of the panel 18 (block 118). If the voltage output of the data approaches the voltage rails, the comparator 37 fires a signal indicative of a fault (e.g., a fault current in the order of 10 mA) to begin fault protection measures. For example, the method 114 includes opening the interface switch 44 to decouple the panel 18 (e.g., data line) from the integrator 34 (block 120). As mentioned above, closing of the switches 108 and 110 sends a signal to open the interface switch 44. Opening of the interface switch 44 also blocks crosstalk across the digital X-ray panel 18 (e.g., between data lines coupled via a common electrode) due to the fault and, thus, reduces image artifacts in generated images. Another fault protection measure includes permanently clamping the faulty data line to the ground voltage to source or sink the fault current (block 122). Additional fault protection measures include resetting the integrator 34 (block 124) via switch 54 and clamping the output of the integrator 34 (block 126). Closing the switch 112 sends a signal to open switches 56 and 58 to clamp the output of the integrator 34.

Technical effects of the disclosed embodiments include providing systems and methods to better regulate signal acquisition between the digital detector X-ray panel 18 and the front-end circuitry (e.g., integrator 34) in response to integrator reset due to switching between pixels of a data line or integrator saturation or in response to a detected fault in the panel 18. In particular, the disclosed embodiments provide the interface switch 44 disposed between the detector panel 18 and the integrator 34 that opens prior to reset of the integrator 34 or upon detection of a fault in the digital X-ray panel. The open interface switch 44 blocks crosstalk between components of the panel 18 due to charge dumping from the integrator 34 or a fault current and, thus, reduces image artifacts in generated images. In addition, interface switch 44 enables additional signal processing of the acquired analog input signal from the panel 18. Further, the interface switch 44 provides additional electrostatic discharge protection between the panel 18 and the front-end circuitry due to junctions formed between the panel 18 and the integrator 34 via the switch 44.

This written description uses examples, including the best mode, to enable any person skilled in the art to practice the disclosed embodiments, including making and using any devices or systems and performing any incorporated methods. The patentable scope of the embodiments is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for regulating the acquisition of an analog input signal from a digital X-ray panel, comprising:
opening a switch disposed between an integrator and the digital X-ray panel prior to an integrator event or upon detection of a fault in the digital X-ray panel to decouple the integrator from the digital X-ray panel, wherein the integrator is configured to integrate the analog input signal from the digital X-ray panel.

2. The method of claim 1, wherein the integrator event comprises a reset of the integrator to an initial condition where an output of the integrator is set to a known reference voltage.

3. The method of claim 2, wherein the reset occurs upon switching between pixels in a data line of the digital X-ray panel.

4. The method of claim 2, wherein the reset occurs upon saturation of the integrator.

5. The method of claim 4, comprising decoupling the integrator from other circuits which store a signal proportional to the output of the integrator.

6. The method of claim 4, wherein the integrator comprises a feedback capacitor, and the method comprises decoupling the feedback capacitor from the integrator prior to the reset.

7. The method of claim 2, comprising coupling a data line of the digital X-ray panel to the reference voltage after opening of the switch and prior to the reset.

8. The method of claim 1, wherein opening of the switch blocks crosstalk across the digital X-ray panel and reduces image artifacts in an image generated from the analog input signal.

9. The method of claim 1, wherein opening of the switch blocks charge dumping from the integrator to the digital X-ray panel.

10. The method of claim 1, comprising detecting the fault in a data line of the digital X-ray panel.

11. The method of claim 10, comprising, upon opening of the switch, clamping the data line to a ground voltage to source or sink a fault current.

12. The method of claim 11, comprising resetting the integrator and clamping an output of the integrator.

13. The method of claim 1, comprising integrating the analog input signal from the digital X-ray panel prior to opening of the switch and averaging multiple readings of an output of the integrator based on the analog output signal after opening of the switch to reduce digitization noise.

14. A digital acquisition system, comprising:
a digital X-ray panel configured to acquire X-ray image data, wherein the digital X-ray panel comprises a plurality of pixels configured to store a charge;
for each pixel, an integrator configured to integrate an analog input signal representative of the charge stored on the respective individual pixel; and
for each integrator, a switch disposed between the respective integrator and the digital X-ray panel, wherein the switch is configured to open to decouple the respective integrator from the digital X-ray panel prior to reset of the respective integrator or upon detection of a fault in the digital X-ray panel.

15. The system of claim 14, wherein the digital acquisition system comprises at least one data line coupled to more than one pixel, and the reset occurs upon switching between the respective pixels coupled to the at least one data line of the digital X-ray panel.

16. The system of claim 15, wherein the reset occurs upon saturation of the respective integrator.

17. The system of claim 14, wherein the switches are configured to provide additional electrostatic discharge protection.

18. The system of claim 14, wherein the switches comprise an ON resistance of approximately 100 Ohm or less.

19. The system of claim 14, wherein opening of the respective switch blocks crosstalk across the digital X-ray panel and reduces artifacts in an image generated from the X-ray image data.

20. The system of claim 14, wherein opening of the respective switch blocks charge dumping from the integrator to the digital X-ray panel.

21. The system of claim 14, wherein the respective integrator is configured to integrate the analog input signal prior to opening of the respective switch and the respective integrator is configured to provide an output based on the analog output signal for digitization after opening of the respective switch to reduce digitization noise.

22. A method for fault protection of a digital X-ray panel, comprising:
detecting a fault in a data line of the digital X-ray panel; and
opening a switch disposed between an integrator and the digital X-ray panel to decouple the integrator from the digital X-ray panel, wherein the integrator is configured to integrate the analog input signal from the digital X-ray panel.

23. The method of claim 22, monitoring the data line of the digital X-ray panel for a fault.

24. The method of claim 22, comprising, upon opening of the switch, clamping the data line to a ground voltage to source or sink a fault current.

25. The method of claim 24, comprising resetting the integrator and clamping an output of the integrator.

* * * * *